United States Patent [19]

Eastman et al.

[11] Patent Number: 4,482,646

[45] Date of Patent: Nov. 13, 1984

[54] OXIDATIVE DEHYDROGENATION OF PARAFFINS

[75] Inventors: Alan D. Eastman; James B. Kimble, both of Bartlesville, Okla.

[73] Assignee: Phillips Petroleum Company, Bartlesville, Okla.

[21] Appl. No.: 586,503

[22] Filed: Mar. 5, 1984

Related U.S. Application Data

[62] Division of Ser. No. 487,366, Apr. 21, 1983, Pat. No. 4,450,313.

[51] Int. Cl.³ .............................................. B01J 23/02
[52] U.S. Cl. ..................................... 502/324; 502/344; 502/350
[58] Field of Search ....................... 502/324, 344, 350; 585/624, 661, 443, 380

[56] References Cited

U.S. PATENT DOCUMENTS

| | | | |
|---|---|---|---|
| 2,795,574 | 6/1957 | Feller et al. | 502/344 |
| 3,210,436 | 10/1965 | Bajars et al. | 585/618 |
| 3,308,191 | 3/1967 | Bajars | 585/619 |
| 3,308,196 | 3/1967 | Bajars | 585/618 |
| 3,308,200 | 3/1967 | Bajars | 585/620 |
| 3,565,829 | 2/1971 | Friedrichsen et al. | 502/344 |
| 3,686,347 | 8/1972 | Dean et al. | 585/625 |
| 3,784,485 | 1/1974 | Tumezsko | 502/344 |
| 4,176,140 | 11/1979 | Bertus et al. | 585/629 |

FOREIGN PATENT DOCUMENTS 0109904  8/1979  Japan ................................. 502/344

*Primary Examiner*—Delbert E. Gantz
*Assistant Examiner*—Cynthia A. Prezlock
*Attorney, Agent, or Firm*—French and Doescher

[57] ABSTRACT

An oxidative dehydrogenation process for a paraffin or mixture of paraffins having from 2 to 5 carbon atoms employing a catalyst composition comprising lithium and titanium. The selectivity of the catalyst composition may be improved by adding manganese to the catalyst composition.

4 Claims, No Drawings

OXIDATIVE DEHYDROGENATION OF PARAFFINS

This application is a division of application Ser. No. 487,366 filed Apr. 21, 1983, now U.S. Pat. No. 4,450,313.

This invention relates to an improved catalytic process for the oxidative dehydrogenation of light paraffins, and a catalyst therefor.

Oxidative dehydrogenation processes for the conversion of paraffins to olefins are well known. However, new catalysts having high selectivity and conversion are always desirable and it is an object of this invention to provide a catalyst composition comprising lithium and titanium which has a high selectivity and conversion for the oxidative dehydrogenation of light paraffins and thus provides an improved process for the oxidative dehydrogenation of light paraffins.

In accordance with the present invention, a paraffin or mixtures of paraffins having from 2 to 5 carbon atoms is oxidatively dehydrogenated in the presence of a catalyst composition comprising lithium and titanium. The selectivity of the catalyst composition may be improved by adding manganese to the catalyst composition.

The dehydrogenation process preferably has alternate reaction periods and regeneration periods. The oxidative dehydrogenation process is carried out under suitable conditions in the presence of free oxygen. The catalyst regeneration process is carried out by terminating the flow of the hydrocarbon feedstock but maintaining the presence of a free oxygen-containing gas to remove carbonaceous materials which may have formed on the catalyst during the oxidative dehydrogenation process.

Other objects and advantages of the invention will be apparent from the foregoing brief description of the invention and the appended claims as well as from the detailed description of the invention which follows.

Paraffins which can be oxidatively dehydrogenated in accordance with the present invention are paraffins which have from 2 to 5 carbon atoms per molecule. The oxidative dehydrogenation process of the present invention is particularly applicable to the conversion of ethane to ethylene.

The oxidative dehydrogenation catalyst employed in the process of the present invention is a composition comprising lithium and titanium. Sufficient oxygen is present in the catalyst composition to satisfy the valence requirements of the lithium and titanium. Manganese may also be present in the catalyst composition to improve the selectivity of the process.

The catalyst composition comprising lithium and titanium may be prepared by intimately mixing suitable portions of a lithium compound and titanium compound, which are in the oxide form or a form which may be directly converted to the oxide form when calcined in the presence of free oxygen, preferably in a liquid such as water. The resulting mixture is dried and then calcined in the presence of free oxygen at a temperature in the range of about 420° C. to about 1100° C., preferably in the range of about 650° C. to about 980° C., to form lithium/titanium catalyst. Suitable lithium compounds are lithium hydroxide, lithium carbonate and lithium nitrate. Suitable titanium compounds are titanium dioxide, titanium oxide and titanium trioxide. For convenience, the titanium compound used in preparing the catalyst composition preferably has extremely fine particle size to promote intimate mixing of the lithium compound and titanium compound. Flame hydrolyzed titanium dioxide has extremely small particle size and is particularly preferred in preparing the catalyst.

The atomic ratio of lithium to titanium can be any suitable ratio but should be above about 1.8:1 to provide a catalyst having an acceptable conversion. The atomic ratio of lithium to titanium will preferably lie in the range of about 2:1 to about 3:1 because the conversion of the catalyst seems to be greatest for atomic ratios of lithium to titanium in this range.

Manganese can be added to the lithium/titanium catalyst prepared in the manner described above by any method known in the art. Any suitable manganese compound which can be converted directly to the oxide form by calcining in the presence of free oxygen can be mixed directly with the lithium/titanium catalyst. However, for ease of preparation, the preferred method of adding the manganese is by impregnating the preformed lithium/titanium catalyst with a solution of manganese nitrate. The impregnated catalyst is dried to remove solvent and is then calcined in air at a temperature in the range of about 420° C. to about 1100° C., preferably in the range of about 650° C. to about 980° C.

The catalyst composition comprising lithium, titanium and manganese may also be prepared by slurrying a solution containing the above-described lithium, manganese and titanium compounds. The resulting slurry is then dried and calcined as previously described for the preparation of the lithium/titanium catalyst.

The concentration of the manganese in the catalyst composition can be any suitable concentration. The concentration of the manganese, expressed as an element, will generally be in the range of about 1 to about 10 weight percent based on the weight of the catalyst composition. More preferably, the concentration of manganese, expressed as an element, will generally be in the range of about 2 to about 3 weight percent based on the weight of the catalyst composition.

The oxidative dehydrogenation process of the present invention is preferably carried out by means of any apparatus whereby there is achieved an alternate contact of the catalyst composition with the paraffin to be dehydrogenated and free oxygen and thereafter of the catalyst with only free oxygen.

Any suitable oxidative dehydrogenation temperature can be employed which provides the desired degree of catalytic activity in the dehydrogenation of the light paraffins. The oxidative dehydrogenation temperature will generally be in the range of about 480° C. to about 815° C. For the oxidative dehydrogenation of ethane the more preferred temperature is in the range of about 620° C. to about 705° C. The preferred temperature for each of the paraffins which may be oxidatively dehydrogenated in accordance with the present invention decreases below the preferred temperature for the oxidative dehydrogenation of ethane within the broad range of temperature as the carbon number of the paraffin feed increases.

The catalytic oxidative dehydrogenation process can be carried out at any suitable pressure. Below pressures at which the product begins to polymerize, the oxidative dehydrogenation process is not greatly affected by reaction pressure. The pressure of the oxidative dehydrogenation reaction can be in the range of from about 10 to about 520 kPa and will more preferably be in the range of from about 100 to about 200 kPa.

Any suitable feed rate for the feedstock can be utilized. The feedstock may comprise a fluid stream containing either one of the light paraffins or a mixture of the light paraffins and the feed stream will also contain free oxygen. The reactant hydrocarbon feed rate expressed as volumes of gas at standard conditions per volume of catalyst per hour (GHSV) will generally range from about 100 to about 2500 with a feed rate of about 500 GHSV being preferred.

Any suitable amount of free oxygen may be mixed with the hydrocarbon-containing portion of the feedstock. Generally, air is utilized to supply the free oxygen and a feed rate of air will generally be in the range of from about 1000 GHSV to about 5000 GHSV with a feed rate of about 1800 GHSV being preferred.

Any suitable oxidative dehydrogenation reaction time for the cyclic process may be utilized in the oxidative dehydrogenation process. The oxidative dehydrogenation reaction time will generally range from about 1 second to about 10 minutes in a cyclic process for maximum conversion and selectivity. Longer times in the range of from about 1 hour to about 24 hours (generally considered a continuous process) may be used if lower conversion and selectivity can be tolerated.

The regeneration of the catalyst may be carried out at the temperature and pressure used in the oxidative dehydrogenation step. The regeneration time will generally be in the range of about one times the length of the oxidative dehydrogention step to about ten times the length of the oxidative dehydrogenation step. About one hour will generally be sufficient in any case.

The following examples are presented in further illustration of the invention.

EXAMPLE 1

Catalysts A-F were prepared by dry mixing various ratios of $Li_2CO_3$ and $TiO_2$ in a mechanical blender. Enough water was added to form a smooth thick slurry and the mixing was continued for about 5 minutes. The resulting slurry was then dried in a forced draft oven at about 125° C. and then calcined in air for 3 hours at 600° C. This calcination was followed by calcining in air for 4 hours at 1000° C. The dried product was crushed and sieved to 20/40 mesh. The lithium to titanium atomic ratio for Catalysts A-F was as set forth in Table I.

TABLE I

| Catalyst | Li/Ti Atomic Ratio |
|---|---|
| A | 0.5 |
| B | 0.8 |
| C | 1.0 |
| D | 1.5 |
| E | 2.0 |
| F | 3.0 |

EXPERIMENTAL RESULTS

Catalysts A-F were used in test runs made in an automated catalyst testing unit as follows: One mL of 20/40 mesh catalyst was mixed with 3 mL of 20/40 mesh quartz chips and placed in a quartz tube microreactor mounted vertically in a controlled temperature furnace. The reactor was operated in a continuous downflow fixed-bed mode.

Ethane was dehydrogenated at atmospheric pressure. The reactor was heated to 650° C. under a flow of nitrogen. Then a feed of 3:1 air:ethane at 2400 gas hourly space velocity (GHSV) was passed into the reactor. After a reaction period of one hour, product from the reactor was collected and sampled by gas chromatography. The results of these analyses are given Table II.

TABLE II

| Catalyst | % Conversion of $C_2H_6$ | % Selectivity to $C_2H_4$ |
|---|---|---|
| A | 2.2 | 100 |
| B | 0.8 | 100 |
| C | 4.5 | 100 |
| D | 1.3 | 100 |
| E | 21.3 | 88 |
| F | 10.6 | 92 |

The results set forth in Table II show a dramatic increase in conversion when the atomic ratio of lithium to titanium reached 2:1. However, at an atomic ratio of 3:1 the conversion appears to have been decreasing and thus the preference for an atomic ratio of lithium to titanium between about 2:1 and about 3:1.

It is believed that the conversion will begin to increase substantially when the atomic ratio of lithium to titanium reaches about 1.8:1. It is not known if there is a high limit on the atomic ratio of lithium to titanium at which the conversion will again drop to the levels demonstrated for the lower ratios in Table II.

EXAMPLE II

Catalyst Preparation

A lithium/titanium catalyst promoted with manganese was prepared by first preparing a lithium/titanium catalyst having an atomic ratio of lithium to titanium of 2.5:1 in the same manner as described in Example I. The thus prepared lithium/titanium catalyst was impregnated with manganese by mixing 1.3 grams of 50 percent $Mn(NO_3)_2$ solution with 15 mL of water and adding the resulting solution to 10 grams of the lithium/titanium catalyst in a porcelain evaporating dish. The thus impregnated catalyst was dried in a forced draft oven at about 125° C. and then calcined in air at 810° C. for 3 hours. The resulting catalyst contained 2 weight percent of manganese, expressed as an element, based on the weight of the total catalyst composition. This catalyst is referred to hereinafter as Catalyst G. An unpromoted portion of the lithium/titanium catalyst utilized to prepare Catalyst G was also calcined in air at 810° C. for 3 hours and is referred to hereinafter as Catalyst H.

EXPERIMENTAL RESULTS

Catalysts G and H were tested for oxidative dehydrogenation of ethane in the same manner as previously described in Example I for Catalysts A-F. Results of the test after a 1 hour reaction period are as set forth in Table III.

TABLE III

| Catalyst | % Conversion of $C_2H_6$ | % Selectivity to $C_2H_4$ |
|---|---|---|
| G | 23.4% | 84.4% |
| H | 46.9% | 74.6% |

Referring now to Table III, it can be seen that the manganese promoted catalysts gave an improved selectivity with respect to the selectivity of the unpromoted lithium/titanium catalyst. It also seems that the additional calcining step of the unpromoted lithium/titanium catalyst had the effect of improving the conversion of the catalyst.

Reasonable variations and modifications are possible within the scope of the disclosure and the appended claims to the invention.

That which is claimed is:

1. A catalyst composition comprising lithium and titanium, wherein the atomic ratio of lithium to titanium is above about 1.8:1.

2. A catalyst composition in accordance with claim 1 wherein the atomic ratio of lithium to titanium in said catalyst composition is in the range of about 2:1 to about 3:1.

3. A catalyst composition in accordance with claim 1 additionally comprising manganese.

4. A catalyst composition in accordance with claim 3 wherein the atomic ratio of lithium to titanium in said catalyst composition is in the range of about 2:1 to about 3:1 and wherein the concentration of said manganese in said catalyst composition is in the range of about 1 weight percent to about 10 weight percent calculated as the element and based on the weight of said catalyst composition.

* * * * *